United States Patent [19]

Frost et al.

[11] Patent Number: 5,798,236
[45] Date of Patent: Aug. 25, 1998

[54] SYNTHESIS OF QUINIC ACID FROM GLUCOSE

[75] Inventors: John W. Frost; Karen M. Draths, both of Lafayette; Timothy L. Ward, Delphi, all of Ind.

[73] Assignee: Genencor International, Inc., Rochester, N.Y.

[21] Appl. No.: 954,623

[22] Filed: Sep. 30, 1992

[51] Int. Cl.$^6$ .................................................. C12P 7/40
[52] U.S. Cl. ................... 435/136; 435/69.1; 435/132; 435/172.3; 435/252.31; 435/252.33; 435/232; 435/320.1; 435/133; 536/23.1; 536/23.2
[58] Field of Search .................... 424/94.4; 435/69.1, 435/71.1, 172.3, 190, 252.3, 252.33, 320.1, 132, 232; 536/22.1, 23.2

[56] References Cited

U.S. PATENT DOCUMENTS 5,168,056  12/1992  Frost et al. ........................... 435/172.3

OTHER PUBLICATIONS

Draths, K.M; Frost, J.W.; *J. Am. Chem. Soc.*, 1990; 112:9630, 1657.
Doctoral Dissertation of Karen Draths (1991) Microbial Biocatalysis: Syntesis of Aromatics from D–glucose Davis et al; *Meth. Enzymol.*; 1995; 2:300.

Mitsuhashi et al; *Biochimica et Biophysica Acta* 1954, 15, 268.

Chemical Abstract, vol. 93, No. 25, 22 Dec. 1980, US Abstract No. 235226n.

K.M. Draths, et al., JACS, vol. 144, No. 24, 18 Nov. 1992, pp. 9725–9726.

Catalogue of Borterin & Borteriphege 17th Edit 1989 p. 111.

Schweizer et al. "Cloning the Guinic Acid (GA) Gene ... " *Gene* 14:23–32 1981.

Pongor, S. 1987. Method in Enyznology 154:450–473.

*Primary Examiner*—Robert A. Wax
*Assistant Examiner*—Nashaat T. Nashed
*Attorney, Agent, or Firm*—Kirsten A. Anderson

[57] ABSTRACT

There are described methods for the synthesis of quinoid organic compounds from a renewable energy source such as glucose. The method comprises enhancing the amount of glucose equivalents introduced into the pathway, blocking the common pathway so as to accumulate dehydroquinate and converting the dehydroquinate to quinic acid.

26 Claims, 5 Drawing Sheets

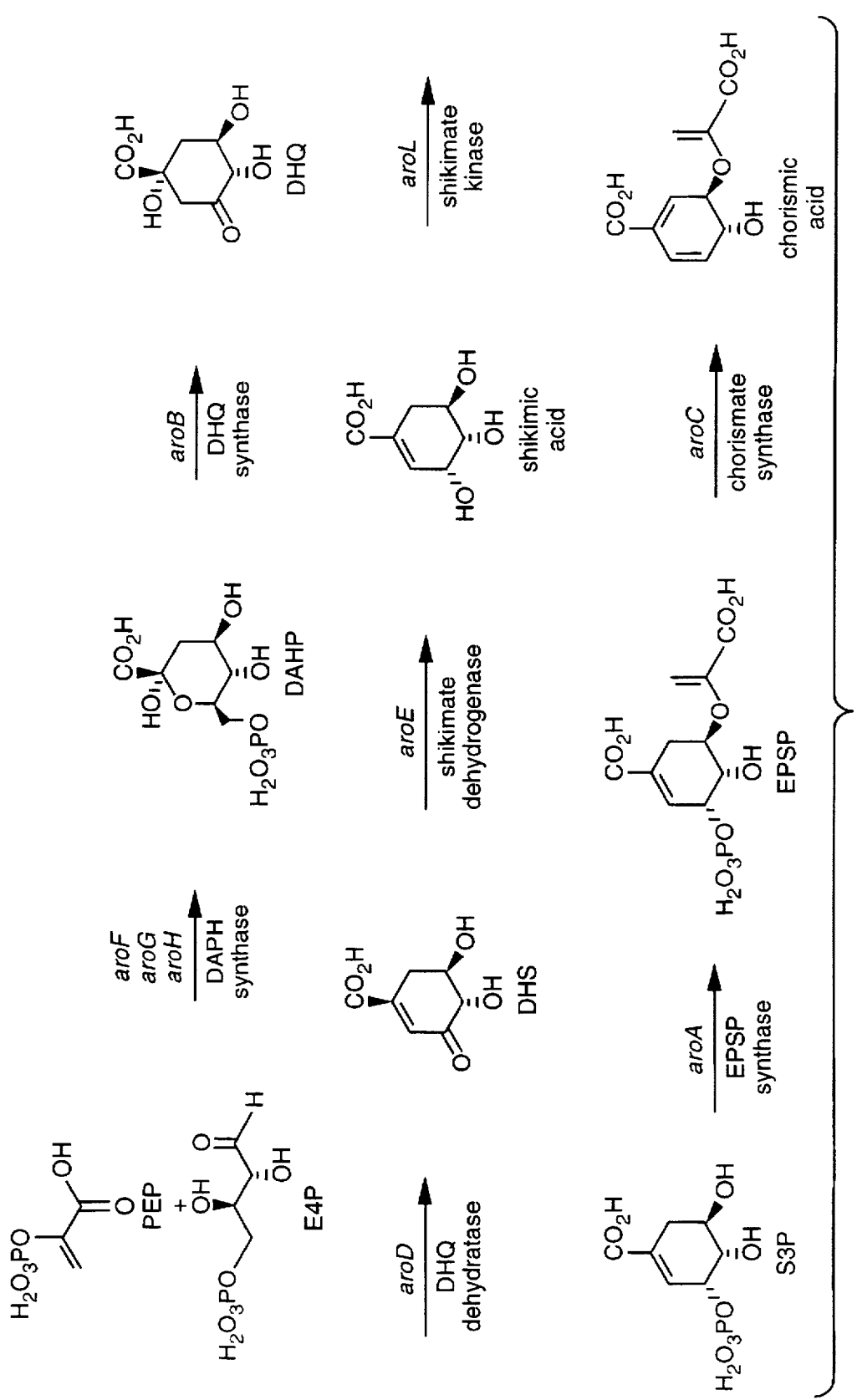
FIG._1

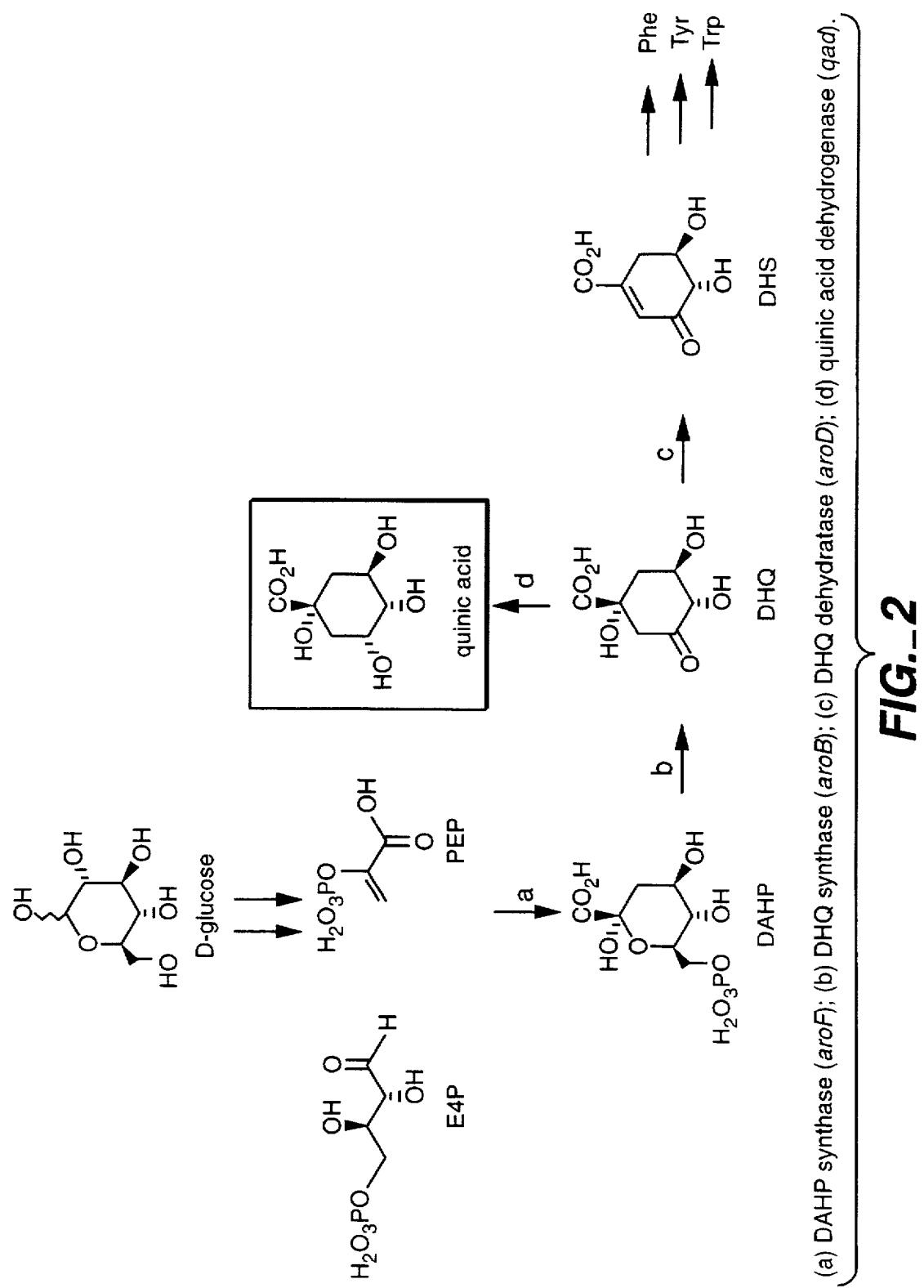
FIG._2
(a) DAHP synthase (aroF); (b) DHQ synthase (aroB); (c) DHQ dehydratase (aroD); (d) quinic acid dehydrogenase (qad).

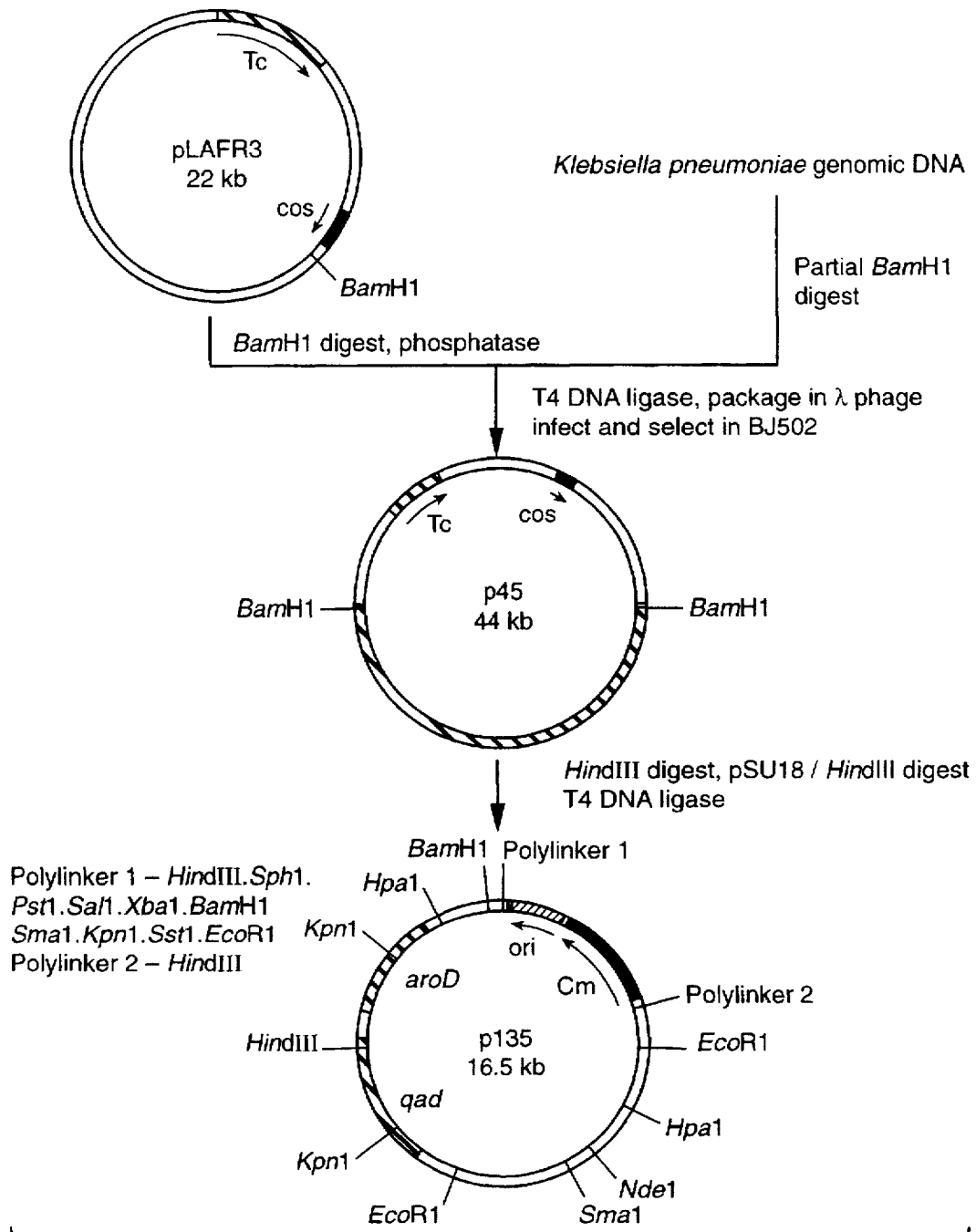
FIG._3A

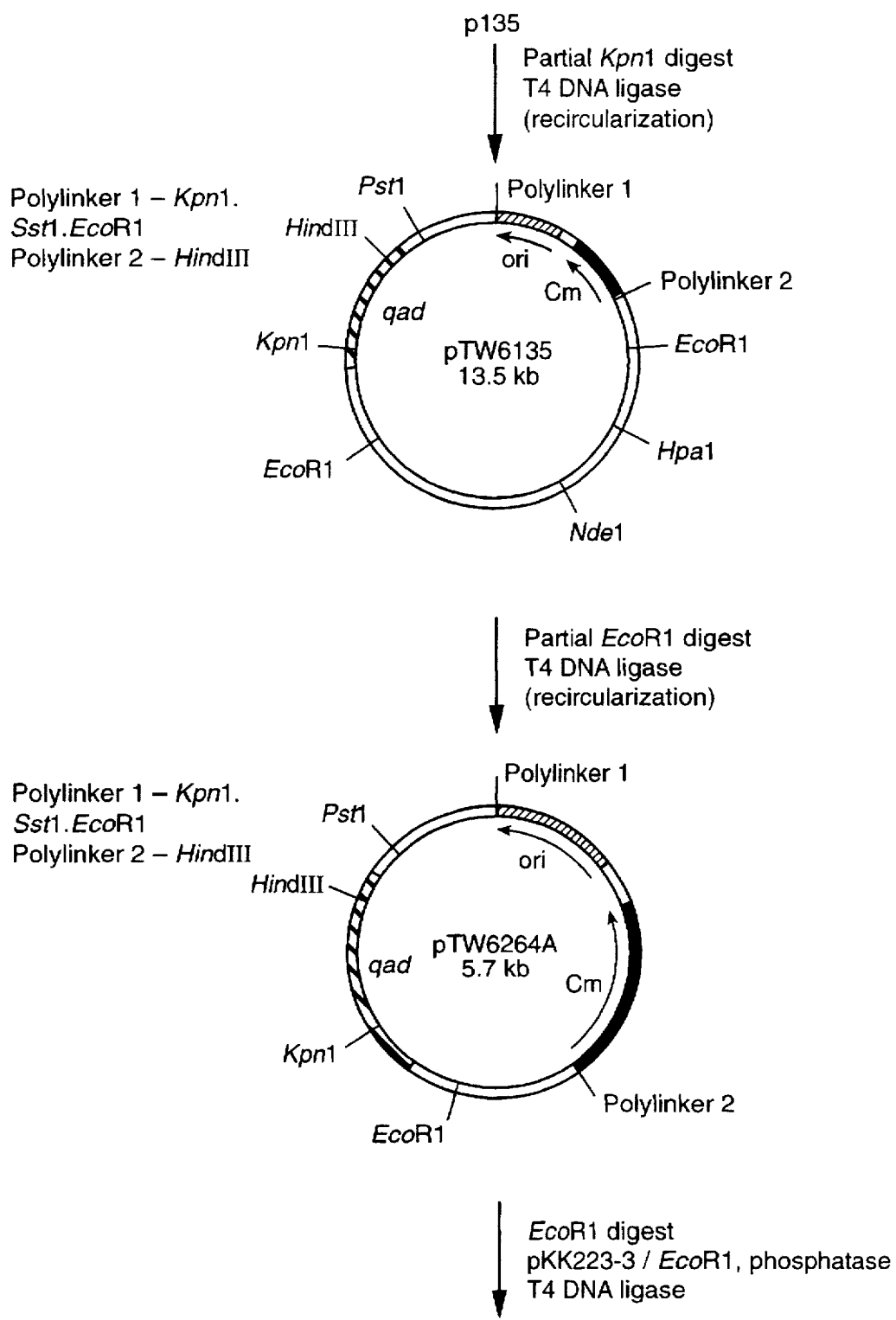
FIG._3B

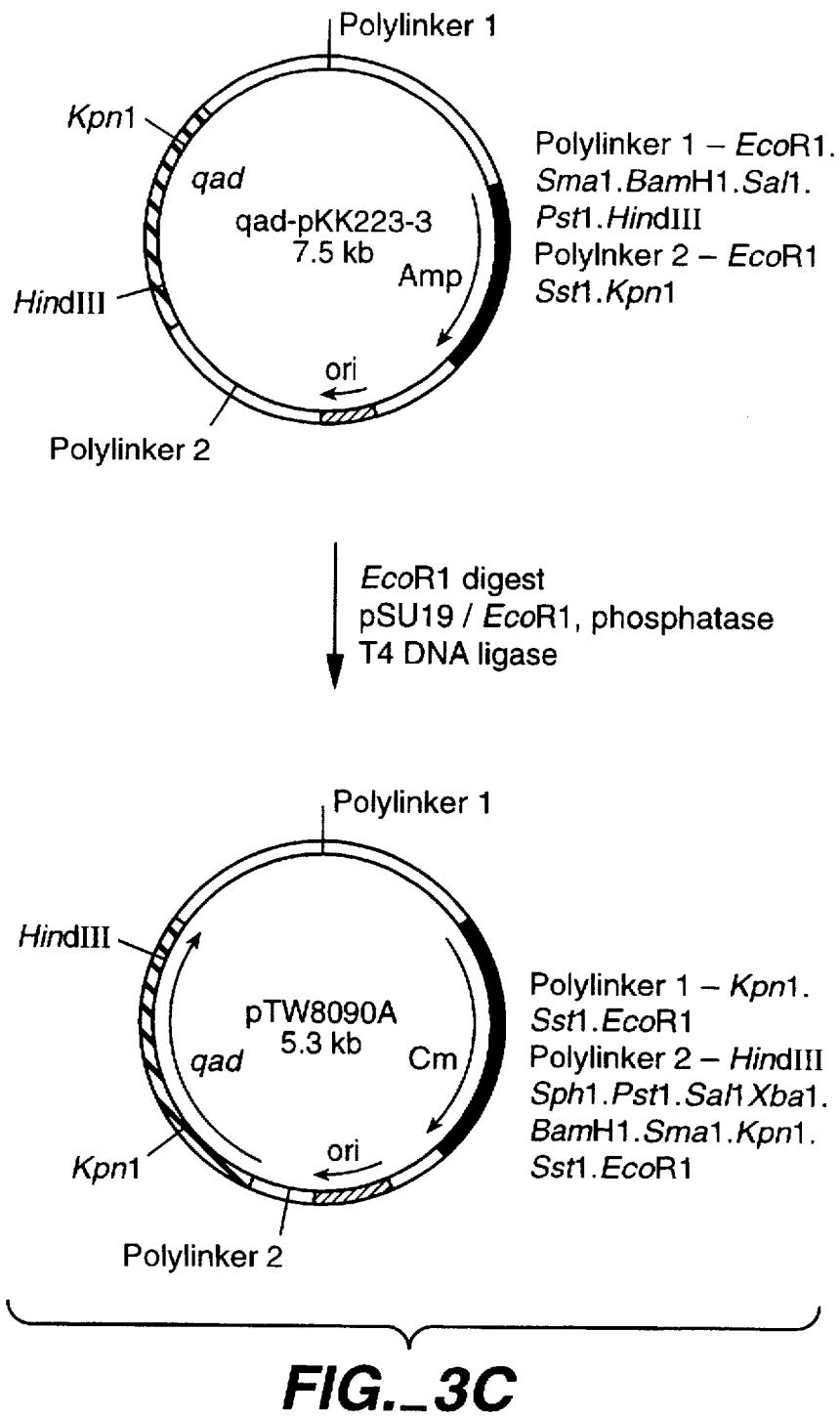
FIG._3C

SYNTHESIS OF QUINIC ACID FROM GLUCOSE

This invention was made with government support under grant #816180-01-0 awarded by the Environmental Protection Agency. The government has certain rights in the invention.

BACKGROUND OF THE INVENTION

This invention relates to the production of quinoid compounds, specifically quinic acid (quinate) and precursors and derivatives thereof by the conversion of a carbon source such as glucose. Both hydroquinone and benzoquinone, which are industrially important organic compounds, can be derived by magnesium (IV) dioxide oxidation of quinic acid. (See Woskrensensky, A., *Justus Liebigs Ann. Chem.*, 1838, 27:257.) Quinic acid is an important molecule utilized as an enantiomerically pure starting material for the synthesis of various synthetic reagents, many of which are biologically important. For example, quinic acid is a useful starting material for the synthesis of FK-506, an immune suppressive agent useful in preventing organ transplant rejection. See Rao, A. V. R., et al., *Tetrahedron Lett.*, 1990, 32(4):547–50. It is also utilized as a convenient source for the synthesis of many natural products that are otherwise difficult to obtain (e.g., mycosporin and D-myo-inositol-1, 4,5-triphosphate, see White, et al., *J. Am. Chem Soc.*, 1989, 111(24):8970–2 and Falck, et al., *J. Org. Chem.*, 1989, 54(25):5851–2, respectively). In addition, quinic acid is utilized as a food additive, resolving agent and is being used experimentally in optical materials.

Quinic acid has previously been isolated from natural sources (e.g., cinchona bark, tobacco leaves, carrot leaves, etc.). However, the cost of isolating quinic acid from such sources precludes its use as an economically viable starting material. In addition, quinic acid has been synthesized chemically, however, such synthesis utilizes solvents, highly reactive reagents and hazardous waste and as such is not environmentally desirable. Therefore, there is a need for a cost effective, environmentally desirable method for the synthesis of quinic acid.

Therefore, it is the intent of the present invention to provide a method for the production of quinic acid, which method utilizes a carbon source as starting material which can be derived from a renewable resource such as corn, sugar beets, sugar cane, or biomass.

SUMMARY OF THE INVENTION

This invention relates to a method for the production of quinic acid and related quinoid organic compounds, such as benzoquinone and hydroquinone, from the common aromatic pathway of a host cell (such as shown in FIGS. 1 and 2), utilizing carbon sources which can be biocatalytically converted to 3-dehydroquinate, for example, glucose. The host cells useful in the present invention can be any microbe capable of converting a carbon source to 3-dehydroquinate.

In a method embodiment of the present invention, there is described a method for the production of a quinoid compound (i.e., quinic acid), the method comprising:

a) selecting a host cell organism capable of synthesizing dehydroquinate;

b) blocking one or more enzymatic reactions in a pathway of the host cell such that the conversion of dehydroquinate to different compounds in the pathway is prevented, provided however that the enzymatic reaction for converting dehydrouquinate to quinic acid is not blocked;

c) optionally, introducing into the host cell the ability to convert dehydroquinate to quinic acid, if such ability is not already present in the host cell; and d) increasing the flow of carbon into the pathway of the host cells; provided that steps b), c) and d) can be carried out in any order or simultaneously.

In an embodiment of the present invention, the carbon flow introduced into the pathway is increased by transforming the host cells with recombinant DNA comprising a gene coding for transketolase, a gene coding for an isozyme of DAHP synthase and a gene coding for 3-dehydroquinate synthase. Plasmid pKD136 carries the genes tkt, aroF, and aroB which encode the enzymes transketolase, the tyrosine-sensitive isozyme of DAHP synthase, and 3-dehydroquinate synthase, respectively. The construction of plasmid pKD136 and expression of pKD136 by *E. coli* has previously been described. (See Draths, K. M; Frost, J. W.; *J. Am. Chem. Soc.*; 1990; 112:9630; which disclosure is incorporated herein by reference.)

Furthermore, the present invention comprises blocking one or more enzymatic reactions in the common aromatic pathway of the host cells (such as shown in FIG. 1), thus preventing the conversion of dehydroquinate to other compounds in the pathway, except that the conversion of dehydroquinate to quinic acid is not blocked (such as shown in FIG. 2). Such blocking action may be carried out by the mutation or deletion (in whole or in part) of the genomic locus (aroD) coding for dehydroquinate dehydratase. Such blocking action, by the deletion or mutation of aroD, ensures that most or all of the carbon flow initially directed into the pathway is directed to the synthesis of quinic acid.

In addition, the present invention comprises converting dehydroquinate to quinic acid. The host cell may have the endogenous ability to convert dehydroquinate to quinic acid (e.g., the host cell has an endogenous gene coding for quinate dehydrogenase). Alternatively, this ability may be the result of transforming the host cells with recombinant DNA comprising a gene coding for quinate dehydrogenase (such as the qad gene). An embodiment of this invention wherein the host cell lacks the ability to carry out this conversion comprises transforming the host cells with the qad gene isolated from *Klebsiella pneumoniae*.

In a preferred embodiment of the present invention the host cell is an *E. coli* strain, and particularly *E. coli* strain AB2848aroD/pKD136/pTW8090AATCC#69086.

BRIEF DESCRIPTION OF THE DRAWINGS

FIG. 1 is a schematic of a common pathway of aromatic biosynthesis.

FIG. 2 is a schematic showing quinic acid as a product of a common aromatic pathway.

FIGS. 3 a, b and c are maps of the isolation of the qad gene from *Klebsiella pneumonia*, resulting in pTW8090A.

DETAILED DESCRIPTION OF THE INVENTION

Common aromatic pathways starting from glucose are known for various microorganisms for the production of various aromatic compounds, for example see FIG. 1 which depicts a pathway which starts from glucose and ultimately leads to chorismate with many intermediates or precursor compounds in the pathway. The enzymes comprised in such pathway include DAHP synthase (aroF), DHQ synthase (aroB), DHQ dehydratase (aroD), shikimate dehydrogenase (aroE), shikimate kinase (aroL), EPSP synthase (aroA) and chorismate synthase (aroC). It has been found that host cells can be induced to feed glucose equivalents into this pathway and/or to block the progression of this pathway whereby dehydroquinate (DHQ) is accumulated.

Enhanced expression of genes coding for proteins able to perform or control the induction of this divergent pathway or common aromatic pathway enzymatic functions is mediated by genetic elements transferable into a host cell. Genetic elements as herein defined include nucleic acids (generally DNA or RNA) having expressible coding sequences for products such as proteins, apoproteins, or antisense RNA, which can perform or control pathway enzymatic functions. The expressed proteins can function as enzymes, repress or derepress enzyme activity, or control expression of enzymes. The nucleic acids coding these expressible sequences can be either chromosomal (e.g., integrated into a host cell chromosome by homologous recombination) or extrachromosomal (e.g., carried by plasmids, cosmids, etc.). In addition, genetic elements are defined to include optional expression control sequences including promoters, repressors, and enhancers that act to control expression or derepression of coding sequences for proteins, apoproteins, or antisense RNA. For example, such control sequences can be inserted into wild-type host cells to promote overexpression of selected enzymes already encoded in the host cell genome, or alternatively can be used to control synthesis of extrachromosomally encoded enzymes.

The genetic elements of the present invention can be introduced into a host cell by plasmids, cosmids, phages, yeast artificial chromosomes or other vectors that mediate transfer of the genetic elements into a host cell. These vectors can include an origin of replication along with cis-acting control elements that control replication of the vector and the genetic elements carried by the vector. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin.

A preferred means for introducing genetic elements into a host cell utilizes an extrachromosomal multi-copy plasmid vector into which genetic elements, in accordance with the present invention, are inserted. Plasmid borne introduction of the genetic element into host cells involves an initial cleaving of a plasmid with a restriction enzyme, followed by ligation of the plasmid and genetic elements, in accordance with the invention. Upon recircularization of the ligated recombinant plasmid, transduction or other mechanism for plasmid transfer is utilized to transfer the plasmid into the host cell. Plasmids suitable for insertion of genetic elements into the host cell include but are not limited to pKD136, p45, p135, pTW6135, pTW6264A, pKK223-3 and pTW8090A.

Suitable host cells for use in the present invention are members of those genera capable of being utilized for industrial biosynthetic production of desired aromatic compounds. Accordingly, host cells can include microbes which are capable of converting a carbon source to 3-dehydroquinate. Preferred host cells are Escherichia coli.

For industrial production of quinic acid and other metabolites derived from the pathway stemming from the chorismate pathway, deregulated mutant strains of the above recited genera that lack feedback inhibition of one or more enzymes in the metabolic biosynthetic pathway may be used.

In a preferred embodiment of the present invention, quinic acid is synthesized by E. coli. This synthesis by E. coli is illustrated in FIG. 2 whereby the pathway is blocked by eliminating the aroD enzyme activity (c in FIG. 2) and introducing the qad gene (d in FIG. 2) into the host cells to convert the dehydroquinate (DHQ) to quinic acid. This modification of the pathway constitutes an important variable to consider in the design of biocatalytic syntheses of aromatic amino acids and related secondary metabolites. Specifically, the modified pathway may be a useful route for converting a carbon source such as glucose into quinic acid, a molecule from which a variety of pharmaceuticals, agrochemicals, flavors, and polymerization inhibitors are industrially derived.

Building on successful efforts to increase the flow of carbon committed to the common pathway or aromatic amino acid biosynthesis in host cells (Escherichia coli), it was thought that introduction of a gene encoding quinate dehydrogenase into Escherichia coli might result in the generation of quinic acid from the shikimate pathway intermediate dehydroquinate. This expectation was based on the equilibrium (Davis, B. D.; Gilvarg, C.; Mitsuhashi, S.; Meth. Enzymol.; 1955; 2:300) of the interconversion of dehydroquinate and quinate catalyzed by quinate dehydrogenase which lies in favor of quinic acid. Since it is not indigenous in Escherichia coli, the quinate dehydrogenase encoding qad gene was isolated from another strain. The Klebsiella pneumoniae mutant strain A170-40 ATCC 25597, deposited with the American Type Culture Collection, 12301 Parklawn Drive, Rockville, Md. 20852, was used. Some bacterial strains, such as Klebsiella pneumoniae, can use quinic acid as its sole carbon source. By virtue of dehydroquinate catabolism, these strains displace the aforementioned equilibrium of the reaction catalyzed by quinate dehydrogenase in the thermodynamically disfavored direction.

Plasmid pKD136 has been shown to significantly increase the number of glucose equivalents (carbon flow) committed to the aromatic amino acid biosynthetic pathway. This plasmid contains the transketolase encoding tkt gene (Draths, K. M., Frost, J. W., J. Am. Chem. Soc., 1990; 112:1657; Draths, K. M., Pompliano, D. L., Conley, D. L., Frost, J. W., Berry, A., Disbrow, G., Staversky, R., Lievense, J., unpublished results), the tyrosine sensitive DAHP isozyme encoding aroF gene (Herrmann, K. M., Amino Acids: Biosynthesis and Genetic Regulation, Herrmann, K. M., Somerville, R. L., Ed., Addison-Wesley: Reading, 1983, Chapter 17; Pittard, A. J., Escherichia coli and Salmonella typhimurium, Neidhardt, F. C., Ed., American Society for Microbiology, Washington, 1987, Vol. 1, Chapter 24; Cobbett, C. S., Morrison, S., Pittard, J., Bacteriol., 1984 157:303; Garner, C. C., Herrmann, K. M., J. Biol. Chem., 1985, 260:3820; Cobbett, C. S., Delbridge, M. L., J. Bacteriol., 1987, 169:2500; Ogino, T., Garner, C., Markley, J. L., Herrmann, K. M., Proc. Natl. Acad. Sci. USA, 1982, 79:5828; Weaver, L. M., Herrmann, K.M., J. Bacteriol., 1990, 172:6581), and the dehydroquinate (DHQ) synthase encoding aroB gene (Draths, K. M., Frost, J. W., J. Am. Chem. Soc., 1990, 112:9630). These enzymes catalyze transformations in the common pathway for aromatic amino acid biosynthesis (FIG. 1).

The quinic acid made by the described process may be converted to other derivatives such as benzoquinone and subsequently to hydroquinone. The conversion to benzoquinone can be achieved by reacting the quinic acid with manganese dioxide and an appropriate acid, such as sulfuric acid, under appropriate conditions. The benzoquinone can be converted to hydroquinone by standard methods known to those skilled in the art.

5

Experimental:

*Escherichia coli* AB2848aroD, an aroD strain, does not exhibit any dehydroquinate dehydratase activity. Strain AB2848aroD/pKD136 with its increased glucose commitment to the aromatic amino acid pathway and metabolic block accumulates dehydroquinate. This construct when transformed with plasmid pTW8090A, which contains the quinate dehydrogenase encoding qad gene, has accumulated the highest concentrations of quinic acid (24 mM) from D-glucose (80 mM).

Isolation of qad Gene

Isolation of the qad gene from *Klebsiella pneumoniae* strain A170-40 was accomplished as illustrated in FIG. 3. Isolation of the genomic DNA via standard protocol (Silhavy, T. J., Berman, M. L., Enquist, L. W., *Experiments with Gene Fusions*, Cold Spring Harbor Laboratory Press, Box 100, Cold Spring Harbor, N.Y. 11724, 1984) was followed by partial BamHI digest and cloning into the cosmid pLAFR3 (Friedman, A. M., Long, S. R., Brown, S. E., Buikema, W. J., Ansubel, F. M., *Gene*, 1982, 18:289). Packaging of the resulting concatamers into lambda phage and subsequent infection of *Escherichia coli* strain BJ502 resulted in a construct which reacquired normal growth rates on minimal media supplemented with quinic acid. Mutant BJ502 lacks 85% of a wild-type strain's transketolase activity. The resulting limitation in D-erythrose-4-phosphate availability causes slow growth on minimal media lacking aromatic supplementation. Growth of BJ502 on glucose was accelerated by the ability of quinate dehydrogenase to convert quinic acid to dehydroquinate which was then biosynthetically converted to the aromatic amino acids needed by BJ502. Plasmid p45 was isolated using this selection scheme.

Construction of pTW8090A

Subcloning of p45 began with HindIII digest and insertion into the expression vector pSU18 (Martinez, E., Bartolomé, B., de la Cruz, F., *Gene*, 1988, 68:159–62; Chang, A. C. Y., Cohen, S. N., *J. Bacteriol.*, 1978, 134(3):1141–56). Transformation of AB2847aroB followed by growth/no growth selection yielded plasmid p135. Growth of AB2847aroB/ p135 on glucose and quinic acid confirmed the presence and expression of the qad gene. However, no accumulation of either dehydroquinate or quinate was detected in AB2848aroD/pKD136/p135. This indicated that p135 also carried a gene encoding dehydroquinate dehydratase (aroD). As a result, plasmid p135 was subcloned by partial KpnI digest and recircularization to afford plasmid pTW6135 which was qad+ aroD–.

Subsequent transformation of AB2848aroD/pKD136 with pTW6135 and growth in rich medium followed by harvesting of cells and resuspension of these cells in M9 minimal medium containing 56 mM glucose (Sambrook, J., Fritsch, E. F., Maniatis, T., *Molecular Cloning: A Laboratory Manual*, $2_{cd}$ Ed., Cold Spring Harbor Laboratory Press, Box 100, Cold Spring Harbor, N.Y. 11724, 1989) resulted in the accumulation of dehydroquinate (9.5 mM) and quinic acid (7.5 mM). Since the insert was still quite large at approximately 11 kb, further subcloning was completed. Partial EcoRI digest of pTW6135 followed by recircularization removed approximately 8.1 kb and afforded pTW6264A. In order to reestablish a sufficient multiple cloning site, pTW6264A was EcoRI digested and the insert cloned into pKK223-3. The resulting qad+ plasmid qad-pKK233-3 was then digested with EcoRI and the insert cloned into pSU19. The resulting plasmid was named pTW8090A and the subsequent construct AB2848aroD/pKD136/pTW8090A when grown in rich media followed by incubation in mini-

6 mal media accumulated the highest levels of quinic acid (24 mM) to date. All of the D-glucose (80 mM) initially present in the culture supernatant was consumed and no dehydroquinate formation was evident.

EXAMPLE 1

Solutions used to grow AB2848aroD/pKD136/ pTW8090A or accumulate quinic acid included M9 medium (per liter: 6 g $Na_2HPO_4$, 3 g $KH_2PO_4$, 0.5 g NaCl and 1 g $NH_4Cl$) and LB medium (per liter: 10 g Bacto tryptone, 5 g Bacto yeast extract, and 10 g NaCl). A 4 L Erlenmeyer with 1 L of LB medium which also contained ampicillin (40 µg/mL) and chloramphenicol (40 µg/mL) was inoculated (0.5% by volume) with an overnight culture of AB2848aroD/pKD136/pTW8090A grown in the same medium. Cells were cultured at 37° C. with agitation (200 rpm) for 12 h. The cells were harvested (10000 g, 10 min, 4° C.), the supernatant decanted, and the cell pellet resuspended in 50 ML of M9 medium. Cells were again harvested (10000 g, 10 min, 4° C.) the supernatant decanted, and the cells resuspended in a 4 L Erlenmeyer with 1 L of M9 medium containing glucose (80 mM), $MgSO_4$ (1 mM), thiamine (50 µg/mL), ampicillin (40 µg/mL) and chloramphenicol (40 µg/mL). This accumulation medium was cultured at 37° C. with agitation (200 rpm) for 72 h. At 72 h, the culture supernatant was spectroscopically analyzed ($^1$H NMR) which indicated that no glucose was present and that quinic acid (24 mM) had been synthesized. The quinic acid present in the culture supernatant was determined to be spectroscopically ($^1$H NMR) identical to 7 quinic acid obtained from commercial sources.

EXAMPLE 2

A stored culture of the strain AB2848aroD/pKD136/ pTW8090A (0.5 mL) was used to inoculate 500 mL of yeast extract medium (15 g/L yeast extract, 24 g/L $K_2HPO_4$, 9.5 g/L $KH_2PO_4$, 5.0 g/L $(NH_4)_2 SO_4$, 0.1 g/L ampicillin) in a 3 L Fernbach flask. Cells were cultured at 35° C. with agitation (150 rpm) for 12 h. The Fernbach culture was then transferred into a 14 L agitated, aerated fermentor containing 5.5 L of minimal salts medium (5.0 g/L glucose, 7.5 g/L $KH_2PO_4$, 2.0 g/L citric acid, 1·2 g/L $H_2SO_4$, 2.0 g/L $MgSO_4·7H_2O$, 0.32 g/L ferric ammonium citrate, 0.02 g/L $Na_2SO_4$, 0.004 g/L $MnSO_4·H_2O$, 0.004 g/L $ZnCl_2$, 0.004 g/L $CoCl_3·6H_2O$, 0.006 g/L $CuSO_4·5H_2O$, 0.32 g/L $FeSO_4·7H_2O$, 0.003 g/L HCl, 0.1 g/L ampicillin) supplemented with the necessary aromatic nutrients (L-tyrosine, L-tryptophan, L-phenylalanine, p-hydroxybenzoic acid, p-aminobenzoic acid, and 2,3-dihydroxbenzoic acid). The fermentation was aerated at 10 L/m. The pH was controlled at 7.0 with 28% aqueous ammonium hydroxide. The temperature was kept at 35° C. The dissolved oxygen concentration was controlled at 20% of air saturation by varying the agitation rate. Antifoam was added as necessary to prevent foaming. When the initial amount of glucose was exhausted, a concentrated glucose solution (700 g/L) was fed starting at 0.32 mL/m. The glucose feed rate was increased exponentially to 1.44 mL/m over the next 12 h and then held constant at 1.44 mL/m. The quinic acid concentration in the broth reached 10.7 g/L (58 mM) after 24 hr of cultivation in the fermentor.

EXAMPLE 3

After removal of the cells (10000 g, 10 min, 4° C.), the crude culture supernatant containing quinic acid (4.8 g, 25 mmol) was added along with concentrated sulfuric acid (25 mL) and technical grade manganese dioxide (200 g, 2.4 mol) to a 3 L round bottom flask fitted with a reflux condenser, overhead stirrer and thermometer. The temperature of the flask contents was raised to 100° C. and held at this temperature for 1 h. After cooling to room temperature, the reaction mixture was filtered and extracted with ethyl acetate. Based on analysis by gas chromatography, a 40% yield of benzoquinone was obtained. Product benzoquinone was found to be identical to authentic material based on $^1$H NMR and gas chromatography coinjection.

What is claimed is:

1. A method for the production of quinic acid and derivatives thereof, including benzoquinone and hydroquinone, the method comprising:
   a) selecting a host cell selected from the species *Escherichia coli*;
   b) blocking in a pathway of the host cell the conversion of dehydroquinate to dehydroshikimate;
   c) introducing into the host cell the ability to convert dehydroquinate to quinic acid in the host cell by introducing a gene coding for quinate dehydrogenase from Klebsiella to the host cell;
   d) increasing the flow of carbon from a renewable carbon source into the pathway of the host cell; and
   e) culturing the host cell in the presence of the renewable carbon source.

2. A method of claim 1 comprising blocking the conversion of dehydroquinate to dehydroshikimate by eliminating or inhibiting dehydroquinate dehydratase activity in the host cell.

3. A method of claim 2 comprising eliminating or inhibiting the dehydroquinate dehydratase activity in the host cell by deleting in whole or in part, the gene coding for dehydroquinate dehydratase or by mutating said gene.

4. A method of claim 2 comprising deleting or mutating the aroD gene.

5. A method of claim 4 wherein the host cell strain is *Escherichia coli* strain AB2848aroD/pKD136.

6. A method of claim 1 comprising introducing a Klebsiella qad gene.

7. A method of claim 6 comprising introducing the qad gene on plasmid pTW6135 or pTW8090A.

8. A method of claim 1 comprising increasing the flow of carbon into the pathway by transforming the host cells with recombinant DNA comprising a gene coding for transketolase, a gene coding for an isozyme of 3-Deoxy-D-arabino-heptulosonate-7-phosphate synthase and a gene coding for 3-dehydroquinate synthase.

9. A method of claim 8 comprising transforming the host cells with the tkt, aroF, and aroB genes.

10. A method of claim 9 wherein the genes are carried on a plasmid, pKD136.

11. A method of claim 1 wherein the strain of *E. coli* is AB2848aroD/pKD136/pTW8090A.

12. A method of genetically transforming a host cell selected from the genus Escherichia capable of synthesizing dehydroquinate from a renewable carbon source to produce a transformant cell capable of producing quinic acid from said renewable carbon source, said transformation comprising:
   a) blocking in a pathway of the host cell the conversion of dehydroquinate to dehydroshikimate;
   b) introducing into the host cell the ability to convert dehydroquinate to quinic acid in the host cell by introducing a gene coding for quinate dehydrogenase from Klebsiella in the host cell; and
   c) increasing the flow of carbon from the renewable carbon source into the pathway of the host cell.

13. A method of claim 12 comprising blocking the conversion of dehydroquinate to dehyroshikimate by eliminating or inhibiting dehydroquinate dehydratase activity in the host cell.

14. A method of claim 13 comprising eliminating or inhibiting the dehydroquinate dehydratase activity in the host cells by deleting in whole or in part the gene coding for dehydroquinate dehydratase or by mutating the gene.

15. A method of claim 14 comprising deleting or mutating the aroD gene.

16. A method of claim 12 wherein *E. coli* strain AB2848aroD/pKD136 is transformed to introduce into the strain the ability to convert dehydroquinate to quinic acid.

17. A method of claim 12 comprising introducing the Klebsiella qad gene.

18. A method of claim 12 comprising increasing the flow of carbon into the pathway of the host cells by transforming the host cells with recombinant DNA comprising a gene coding for transketolase, a gene coding for an isozyme of 3-Deoxy-D-arabino-heptulosonate-7-phosphate synthase and a gene coding for 3-dehydroquinate synthase.

19. A method of claim 18 comprising transforming the host cells with the genes tkt, aroF, and aroB.

20. A cell transformant prepared according to the method of claim 12.

21. *E. coli* strain AB2848aroD/pKD136/pTW8090A, ATCC #69086 deposited at the American Type Culture Collection, 6301 Parklawn Drive, Rockville, Md. 20852, on Oct. 19, 1992.

22. A cell transformant of a host species selected from *E. coli* characterized by the constitutive expression of exogenous genes tkt, aroF, aroB and Klebsiella qad and the absence of dehydroquinate dehydratase activity.

23. A method for producing quinic acid from a carbon source comprising culturing a cell transformant of claim 21, or 20 in the presence of the carbon source.

24. An isolated chromosomal or extrachromosomal genetic element comprising one or more copies of Klebsiella qad.

25. Plasmid pTW6135.

26. A genetic element comprising a tkt gene, an aroF gene, an aroB gene and a Klebsiella qad gene.

* * * * *